United States Patent
Dani et al.

(10) Patent No.: US 10,227,616 B2
(45) Date of Patent: Mar. 12, 2019

(54) PROCESS FOR THE PRODUCTION OF 1,4-BUTANEDIOL

(71) Applicants: Novamont S.p.A., Novara (IT); Genomatica, Inc., San Diego, CA (US)

(72) Inventors: Maria Dani, Capua (IT); Giuseppe Ruggiero, San Nicola La Strada (IT); Davide Perini, Romentino (IT); Alice Bianchi, Assago (IT)

(73) Assignees: Novamont S.P.A., Novara (IT); Genomatica, Inc., San Diego, CA (US)

( * ) Notice: Subject to any disclaimer, the term of this patent is extended or adjusted under 35 U.S.C. 154(b) by 323 days.

(21) Appl. No.: 15/303,931

(22) PCT Filed: Apr. 14, 2015

(86) PCT No.: PCT/EP2015/058080
§ 371 (c)(1),
(2) Date: Oct. 13, 2016

(87) PCT Pub. No.: WO2015/158716
PCT Pub. Date: Oct. 22, 2015

(65) Prior Publication Data
US 2017/0029852 A1    Feb. 2, 2017

(30) Foreign Application Priority Data

Apr. 16, 2014 (IT) .............................. MI2014A0710

(51) Int. Cl.
*C12P 7/18* (2006.01)

(52) U.S. Cl.
CPC ...................................... *C12P 7/18* (2013.01)

(58) Field of Classification Search
None
See application file for complete search history.

(56) References Cited

U.S. PATENT DOCUMENTS

2015/0148513 A1    5/2015    Pharkya et al.

FOREIGN PATENT DOCUMENTS

| WO | WO-2011/154503 A1 | 12/2011 |
| WO | WO-2013/184602 | 12/2013 |

OTHER PUBLICATIONS

Yim et al., "Metabolic engineering of *Escherichia coli* for direct production of 1,4-butanediol", Nature Chemical Biology, vol. 7, Jul. 2011, 445-452.
Wang et al., "Succinate production from different carbon sources under anaerobic conditions by metabolic engineered *Escherichia coli* strains", Metabolic Engineering, vol. 13 N. 3, (2011) 328-335.

*Primary Examiner* — Suzanne M Noakes
*Assistant Examiner* — Jae W Lee
(74) *Attorney, Agent, or Firm* — Polsinelli PC

(57) ABSTRACT

Process for the synthesis of 1,4-butanediol comprising fermentation of a culture medium by a microorganism provided with at least one metabolic pathway for the synthesis of 1,4-butanediol and able to use saccharose, in which said culture medium comprises a glucose and saccharose mixture comprising, based on the combined weight of glucose and saccharose, 10-90% by weight of saccharose and 10-90% by weight of glucose.

20 Claims, No Drawings

PROCESS FOR THE PRODUCTION OF 1,4-BUTANEDIOL

CROSS REFERENCE TO RELATED APPLICATIONS

This application is a National Phase filing under 35 U.S.C. § 371 of PCT/EP2015/058080 filed on Apr. 14, 2015; and this application claims priority to Application No. MI2014A000710 filed on Apr. 14, 2014 in Italy. The entire contents of each application are hereby incorporated by reference.

This invention relates to a process for the production of 1,4-butanediol via the fermentation route that has considerable advantages from the viewpoint of flexibility, reliability and economy.

1,4-butanediol is a very well-known chemical intermediate widely used as a solvent and comonomer for the production of various types of products, such as, for example, polyesters of the diacid-diol type, among which polybutylene terephthalate, polybutylene succinate, polybutylene sebacate, and poly(butylene sebacate-co-butylene terephthalate).

Today, 1,4-butanediol is substantially obtained from raw materials of petrochemical origin, among which acetylene, maleic anhydride, propylene oxide.

The search for technologies that aim to safeguard petroleum resources through the ever increasing use of renewable raw materials, on the one hand, and the progressive dissemination of biotechnologies, on the other, has led to the search for processes to obtain 1,4-butanediol from a renewable source through fermentation processes starting from carbohydrates of various kinds, such as, for example, sugars and lignocellulosic biomasses.

For example, WO 2008/115840 describes a method for the synthesis of 1,4-butanediol through a fermentation process starting from carbohydrates that comprises the use of strains of *Escherichia Coli* genetically modified to express metabolic pathways for the biosyntheses of 1,4-butanediol.

WO 2009/023493 describes a process for the production of 1,4-butanediol starting from carbohydrates by means of a strain of *Escherichia coli* comprising a set of metabolic modifications comprising the destruction of one or more endogenous genes.

WO 2010/030711 describes genetically modified microorganisms provided with metabolic pathways for the synthesis of 1,4-butanediol in the presence of 4-hydroxybutyrate starting from carbohydrates of various types.

However, there is much variability in performance levels between different raw materials, and this in general leads to lesser flexibility of the fermentation processes.

For the synthesis of 1,4-butanediol, for example, glucose, a monosaccharide easy for microorganisms to assimilate, is considered an excellent substrate that guarantees yields and productivity generally higher than those of saccharose. Glucose, however, has the disadvantage of being a much more expensive raw material than saccharose in some parts of the world, thus making its use significantly less competitive. Saccharose is, moreover, a disaccharide which, for the synthesis of 1,4-butanediol, compared to glucose, requires the use of additional transporter enzymes, for example the disaccharide hydrolysis reaction to give glucose and fructose.

Added to this is the fact that fermentation broths typically comprise, besides high quantities of cell bodies and water, by-products, salts and nutrients present in the fermentation medium, unfermented sugars, and other impurities possibly present in the starting materials. Said components may, in fact, react with 1,4-butanediol or can promote reactions of decomposition to tetrahydrofuran, thus lowering the quality of the product and the final yield of the process. In the current state, therefore, there is a need to improve the processes for fermentative synthesis of 1,4-butanediol from the viewpoint of economy, productivity, reliability and quality of the products, so as to render them more competitive compared to conventional chemical synthesis processes.

Starting from this technical problem, it has now surprisingly been discovered that, if glucose and saccharose mixtures comprising, with respect to the sum of the combined weight of glucose and saccharose, 10-90% by weight, preferably 30-80% by weight, more preferably 40-70% by weight, even more preferably 45-65% by weight of saccharose and 10-90% by weight, preferably 20-70% by weight, more preferably 30-60%, even more preferably 35-55% by weight of glucose are used as the substrate for the fermentation of microorganisms provided with metabolic pathways for the synthesis of 1,4-butanediol, it is possible to obtain fermentation performances (yields, productivity and titre) comparable to, or even greater than, those obtainable using glucose alone, allowing at the same time greater flexibility and reliability of the fermentation process.

Without wishing to be tied to any specific theory, it is in fact felt that, by using such mixture comprising saccharose and glucose, a high level of productivity of 1,4-butanediol can be obtained together with an higher microbic growth, thereby allowing the fermentation processes in which this mixture is used to attain better performance levels than those in which the single constituents of the same are used.

Moreover, with saccharose being a less expensive raw material than glucose in some parts of the world, use of said mixtures can contribute to lowering the costs of running these processes, thus making them more competitive.

Further, the possibility of using a mixture of different raw materials, maintaining substantially unchanged, or possibly improving, the performance levels of the 1,4-butanediol synthesis process, also contributes to making said biotechnological processes more flexible and less subject to limitations of shortages of a raw material.

The present invention, therefore, relates to a process for the synthesis of 1,4-butanediol comprising fermentation of a culture medium by a microorganism provided with at least one metabolic pathway for the synthesis of 1,4-butanediol and able to use sucrose, in which said culture medium comprises a glucose and saccharose mixture comprising, based on the combined weight of glucose and saccharose, 10-90% by weight, preferably 30-80% by weight, more preferably 40-70% by weight, even more preferably 45-65% by weight of saccharose and 10-90% by weight, preferably 20-70%, more preferably 30-60%, even more preferably 35-55% by weight of glucose.

In particular, this invention relates to a process for the synthesis of 1,4-butanediol comprising the steps of:

i. production of 1,4-butanediol through fermentation of a culture medium comprising a glucose and saccharose mixture comprising, based on the combined weight of glucose and saccharose, 10-90% by weight, preferably 30-80% by weight, more preferably 40-70% by weight, even more preferably 45-65% by weight of saccharose and 10-90% by weight, preferably 20-70% by weight, more preferably 30-60%, even more preferably 35-55% by weight of glucose, by a microorganism provided with at least one metabolic pathway for the synthesis of 1,4-butanediol and able to use saccharose;

ii. purification of the 1,4-butanediol obtained in phase i.

The culture medium comprises the glucose and saccharose mixture, which provides the source of carbon necessary for the synthesis of 1,4-butanediol. For the process according to this invention, the culture medium further comprises the substances necessary for the growth and sustenance of the microorganism during the fermentation step, providing it with elements such as, for example, C, H, O, N, K, S, P, Fe, Ca, Co, Mn, Mg. Typically, the culture medium, besides the glucose and saccharose mixture, can contain one or more of the following components: sugars other than saccharose and glucose, protein hydrolysates, proteins, amino acids, organic acids, vitamins, mineral salts, yeast extracts, microelements such as for example Cobalt, Calcium, Copper. When presents, sugars different from saccharose and glucose amount preferably up to 20 wt % with respect to the total amount of sugars in the culture medium (i.e. including saccharose, glucose and sugars other saccharose and glucose), more preferably up to 15 wt %, even more preferably up to 10 wt %, even more preferably up to 8 wt %, even more preferably up to 5 wt %, even more preferably up to 2 wt %. Cobalt, Calcium, Copper may be dosed in the culture medium for example as salts like Cobalt chloride, calcium chloride, copper chloride.

Generally, the glucose and saccharose mixture is present in the culture medium in a concentration of 10-100 g/L, preferably of 15-60 g/L. Since during the fermentation step of the present process the microorganism consumes (uptakes) said mixture, it is necessary to top it up inside the fermentation reactor. This topping up may be carried out in a continuous or discontinuous manner, according to methods known to those skilled in the art. Furthermore, in order to limit the amount of unused sugars and thus to optimize the cheapness of the process, the feeding of the glucose and saccharose mixture is advantageously blocked or gradually decreased before the end of the fermentation. This further allows to simplify the purification steps in step ii of the present process.

Regarding the other components of the culture medium, the culture medium to use in the process according to this invention in general contains salts, trace minerals, sugar and anti-foaming agent.

The culture medium to use in the process according to this invention can be prepared according to any method known to those acquainted with the sector art, for example, mixing all its components together or premixing all the components with the exception of glucose and saccharose and adding the latter at another time, singularly or already premixed in turn. It is also possible to use as the point of departure a culture medium readily available on the market and suitably modify its composition at a later time, for example, at the time of putting the culture medium in contact with the microorganism provided with at least one metabolic pathway for the synthesis of 1,4-butanediol. Typical examples of culture media readily available on the market and suitable for use for this purpose are M9, M63 and Minimal A Media.

In the process according to this invention, before the start of fermentation or in a preliminary step thereof, it is possible to put the microorganism in contact with any appropriate culture medium, whether or not containing the glucose and saccharose mixture, in order to promote its microbic growth. Said step can be repeated one or more times according to requirements, in order to ensure an appropriate microbic content during fermentation.

During fermentation according to the process of the present invention, the whole constituted by the microorganism and by the culture medium containing the glucose and saccharose mixture is maintained in suitable conditions to take advantage of the metabolic pathway for the synthesis of 1,4-butanediol. This may be obtained by operating, for example, under the following conditions: agitation rate at 800-900 rpm, air flow 0.4-1 Pa*m$^3$/s; pH 6-7, temperature 30-37° C.

Those skilled in the art are, moreover, in a position to verify the progress of the process in the course of fermentation, for example, by monitoring the above mentioned operative conditions, if necessary intervening on them to bring the process back into conditions suitable for the production of 1,4-butanediol.

Regarding the microorganism, this is provided with at least one metabolic pathway for the synthesis of 1,4-butanediol and is able to use saccharose, advantageously by means of at least one operon for the assimilation of saccharose.

Regarding the said metabolic pathway for the synthesis of 1,4-butanediol, it can be present in the microorganism in the natural state or can be created artificially, for example, by altering, modifying, amplifying, eliminating, limiting metabolic pathways already existing in the microorganism, inserting therein genetic material from one or more other organisms, inducing spontaneous genetic mutations, adding, during the process, chemical compounds that inhibit or stimulate the said metabolic pathway, or exploiting any genetic engineering technique. Microorganisms provided with metabolic pathways for the synthesis of 1,4-butanediol are known to the skilled in the art and are, for example, described in Yim, H. et al., *Nature Chemical Biology*, Vol. 7, July 2011, pages 445-452 (hereinafter "Yim et al. 2011") and in patent applications WO 2008/115840, WO 2009/023493, WO 2010/030711, WO 2010/071697, WO 2010/141780, WO 2010/141920, WO 2011/031897, WO 2011/047101, WO 2011/066076, WO 2012/177943, AU 2013/3204409, AU 2013/3204038, AU 2013/202623, AU 2013/203176, AU 2013/203177, AU 2013/203342, AU 2013/203440, AU 2013/203480, AU 2013/203163. Particularly preferred metabolic pathways to 1,4-butanediol (BDO) or its intermediate 4-hydroxybutanoic acid (4-HB) include the following. Preferred 4-hydroxybutanoic acid (4-HB) biosynthetic pathway allowing production of 4HB comprise a 4-hydroxybutanoate dehydrogenase, a succinyl-CoA synthetase, a CoA-dependent succinic semialdehyde dehydrogenase, or an α-ketoglutarate decarboxylase. Preferred combined 4-HB and BDO biosynthetic pathways that enable BDO biosynthesis comprise a 4-hydroxybutanoate dehydrogenase, a succinyl-CoA synthetase, a CoA-dependent succinic semialdehyde dehydrogenase, a 4-hydroxybutyrate:CoA transferase, a 4-butyrate kinase, a phosphotransbutyrylase, an α-ketoglutarate decarboxylase, an aldehyde dehydrogenase, an alcohol dehydrogenase or an aldehyde/alcohol dehydrogenase. Additional details are provided in WO2008115840A2 titled "Compositions and methods for the biosynthesis of 1,4-butanediol and its precursors"; particularly FIG. 2 and preferred pathways comprising steps 1,6,7,9,12,13; 1,6,7,10,11,12,13; 3,6,7,9,12,13; 3,6,7,10,11, 12,13; 8,7,9,12,13; 8,7,10,11,12,13; 4/5,7,9,12,13; and 4/5, 7,10,11,12,13 and the detailed enzyme information provided therein. With respect to FIG. 2 of WO2008115840A2 and the preferred pathways recited above, enzymes catalyzing the biosynthetic reactions are: (1) succinyl-CoA synthetase; (2) CoA-independent succinic semialdehyde dehydrogenase; (3) α-ketoglutarate dehydrogenase; (4) glutamate: succinate semialdehyde transaminase; (5) glutamate decarboxylase; (6) CoA-dependent succinic semialdehyde dehydrogenase; (7) 4-hydroxybutanoate dehydrogenase; (8) α-ketoglutarate decarboxylase; (9) 4-hydroxybutyryl CoA:

acetyl-CoA transferase; (10) butyrate kinase; (11) phosphotransbutyrylase; (12) aldehyde dehydrogenase; (13) alcohol dehydrogenase.

With regard to the operon for the assimilation of saccharose, it can be present in the microorganism in the natural state or, if necessary, can be created artificially, for example, by altering, modifying, amplifying, eliminating, limiting metabolic pathways already existing in the microorganism, inserting therein genetic material from one or more other organisms, inducing spontaneous genetic mutations, adding, during the process, chemical compounds that inhibit or stimulate the said metabolic pathway, or exploiting any genetic engineering technique.

The operon necessary for the assimilation of saccharose usually works under the control of a regulatory protein. In accordance with this invention, by "operon" is meant also associations of more than one operons operating under the control of a single regulatory protein (so-called "regulon") as well as a set of more regulons (so-called "modulon").

Microorganisms applicable to the fermentation process according to the present invention may be selected from bacteria, yeasts, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichiapastoris*. In a preferred embodiment of the process, the microorganism belongs to a strain of the species *Escherichia coli*, since it is a well characterized microorganism, suitable for genetic engineering. Other particularly useful host organisms include yeast such as *Saccharomyces cerevisiae*.

In the case of *Escherichia coli*, examples of preferred operons suitable to allow the assimilation of saccharose are the scr regulon from the *Escherichia coli* strain H155, where the enzymatic complex responsible for the assimilation of saccharose comprises the phosphoenolpytuvate:sugar phosphotransferase system, and the regulon csc of the *Escherichia coli* strain W, consisting of a sucrose permease (cscB), D-fructokinase (cscK), saccharose hydrolase (cscA) and a LacI-related sucrose-specific repressor (cscR). An example of *Escherichia coli* strain wherein the csc regulon of the *E. coli* strain W has been inserted is described in Yim H. et al, Nature Chemical Biology, Vol. 7, July 2011, pag. 445-452.

In a particularly preferred embodiment of the invention, the microorganism suitable for the process according to the present invention belongs to a strain of the species *Escherichia coli* and is able to use saccharose by means of at least one operon selected from the scr regulon from the *Escherichia coli* strain H155 and the regulon csc of the *Escherichia coli* strain W. In the step ii of the process according to the invention, 1,4-butanediol is separated from the remaining reaction broth, that comprises among other things the microorganism, cell residues, possibly unreacted sugars, by-products, metabolites and possible components of the culture medium not assimilated or metabolized by said microorganism.

The purification step of 1,4-butanediol can be carried out according to any one of the processes known to those skilled in the art, for example according to the processes described in patent applications WO 2010/141780 and AU 2013/203342.

In one embodiment of the process according to the present invention, step ii for the purification of 1,4-butanediol comprises:
a first step (ii-a) in which the reaction means deriving from the fermentation is separated in a liquid fraction containing 1,4-butanediol and one or more solid fractions and
a second step (i-b) in which the said liquid fraction obtained is further purified.

Regarding the step (ii-a), the solid fractions in general contain the microorganism, cell residues, possibly unreacted sugars, by-products, mineral salts, metabolites and possible components of the culture medium not assimilated or metabolized by said microorganism. In accordance with this invention, by "solid fractions" is meant also suspensions, sludges (also called "slurry") and any fraction having sufficiently high density to separate from a supernate. In this first step of separation, it is possible to treat the reaction means coming from the fermentation with one or more treatments chosen from among settling, centrifugation, filtration, microfiltration, nanofiltration, ultrafiltration, osmosis, other suitable techniques of solid/liquid separation and combinations thereof. For example, the reaction means can first be centrifuged and subsequently filtered, microfiltered, nanofiltered, ultrafiltered and finally osmotised.

In this step of separation, it is, moreover, possible to provide for one or more evaporation operations of the reaction medium or the various intermediate fractions, to eliminate part of the water present therein, thereby contributing to minimize the volumes of the separation equipment. In step (i-b) the liquid fraction obtained in step (ii-a) is further purified for example treating the liquid fraction containing 1,4-butanediol with one or more treatment chosen from among evaporation, distillation, grinding, crystallization and combinations thereof. Said purification can be carried out, for example, by using equipment that exploits the different volatility of the components of the liquid phase containing 1,4-butanediol. In one embodiment, said liquid phase containing 1,4-butanediol is fed to one or more items of equipment to:
(ii-b-1) separate, by means of heating, at least one vapour phase and at least one condensate;
(ii-b-2) condense at least one part of said at least one vapour phase, obtaining a final composition essentially comprising 1,4-butanediol.

The invention is now described with some examples to be understood as being purely illustrative, and not exhaustive, of the same.

EXAMPLES 1-3

A sample of *Escherichia coli* ECKh-436 (see Yim et al. 2011) provided with a metabolic pathway for the synthesis of 1,4-butanediol and in which the regulon csc of the *E. coli* W strain, was inoculated in 50 ml of a first culture medium (10 g/l of Tryptone enzymatic digest from casein Sigma 5 g/l, Yeast extract Sigma, 0.5 g/l NaCl, 10 g/l glucose) in a 250 ml flask. The culture medium together with the microorganism was then stirred at 275 rpm, at a temperature of 37° C., for one night, obtaining a preinoculum.

Subsequently, an amount of 6 ml of the said preinoculum was transferred to a 250 ml flask containing 50 ml of a second culture medium (12.78 g/l Modified M9 Minimal Salt Tecknova, 10 g/l glucose, 1 ml/l $MgSO_4$ 1M, 1 ml/l CaCl$_2$ 0.1 M, 1 ml/l Trace Elements Tecknova T1001, 0.5 ml/l Streptomycin 100 sulphate salt Sigma).

The flask was incubated at 35° C., stirring the contents at 275 rpm for 8-9 hours. After this incubation period, the culture was subdivided into three lots, used for three fermentation tests. In each of the three tests, one lot was used to inoculate a 2 liters bioreactor Biostat B+ (Sartorius Stedim Biotech), filled with 1 liter of a culture medium of different composition:

Example 1 (Comparative)

culture medium composition: 970 ml/l water, 1.73 g/l KH2PO4, 0.83 g/l (NH4) 2SO4, 0.3 g/l Na2SO4, 0.038 g/l calcium citrate, 0.2 g/l citric acid, 2 ml/l MgSO4 1 M, 2 ml/l Trace Elements Tecknova T1001, 0.1 ml/l Antifoam 204 Sigma, 20 g/l glucose).

Example 2 (Comparative)

culture medium composition: 970 ml/l water, 1.73 g/l KH2PO4, 0.83 g/l (NH4) 2SO4, 0.3 g/l Na2SO4, 0.038 g/l calcium citrate, 0.2 g/l citric acid, 2 ml/l MgSO4 1 M, 2 ml/l Trace Elements Tecknova T1001, 0.1 ml/l Antifoam 204 Sigma, 20 g/l saccharose).

Example 3 culture medium composition: 970 ml/l water, 1.73 g/l KH2PO4, 0.83 g/l (NH4) 2SO4, 0.3 g/l Na2SO4, 0.038 g/l calcium citrate, 0.2 g/l citric acid, 2 ml/l MgSO4 1 M, 2 ml/l Trace Elements Tecknova T1001, 0.1 ml/l Antifoam 204 Sigma, 10 g/l glucose, 10 g/l saccharose).

In all three tests, the bioreactor was maintained in the following conditions: stirring 875-825 rpm, air flow at 0.6755 Pa*m$^3$/s, pH 6.75 and temperature 37° C.

The attainment of an optical density at 600 nm (OD$_{600\ nm}$) equal to approximately 4 was in every case considered as the beginning of the step (i) of the process (Elapsed Fermentation Time). In the course of the fermentations, the concentration of sugars presents in the reaction means was continuously maintained in the interval 30-60 g/l for 28 hours from the beginning of the step (i), reducing it progressively up to obtain a concentration of the sugars at the end of the fermentation of about 0 g/L.

At various times, moreover, samples of the reaction means were taken to evaluate the production of 1,4-butanediol. HPLC analyses were performed to determine 1,4-butanediol. The analysis was performed as disclosed in Yim et al. 2011 using an API3200 triple quadrupole system (AB Sciex, Life Technologies, Carlsbad, Calif.), interfaced with Agilent 1200 HPLC, utilizing electrospray ionization and MRM based acquisition methods. BDO and internal standard (1,5-pentanediol or isoleucine) were monitored in positive ionization model. Chromatographic separation was conducted on Zorbax Eclipse XDB C18 4.6×30 mm, 1.8 um particle size, maintaining column at 40° C., flow rate 0.6 mL/min. Injection volume was 3-5 uL. Eluents consisted of water with 0.1% formic acid and methanol with 0.1% formic acid, and fast 0.5 min 5-95% methanol gradient was used, resulting in 3 min long methods. Filtered samples were diluted in water, containing internal standards, dilution factor varied from 200 to 10,000 depending on concentration of BDO.

All three fermentations were considered concluded 32 hours after attainment of OD 4.

The above procedure was repeated twice obtaining, for each Example, three replicas of the fermentation process.

Based on the data collected, average Titre, Yield and Productivity and the growth rate of the microorganisms (μ) (Table 1) were determined for the fermentation processes of Examples 1-3, where "Titre" (g/l) corresponds to the average weight concentration of 1,4-butanediol in the reaction means at the end of the 32 hours of fermentation;

"Yield" (g/g) corresponds to the average yield of the synthesis reaction of 1,4-butanediol, calculated as follows: grams of 1,4-butanediol/grams of sugars uptaken by the microorganism "Productivity" (g/l/h) corresponds to the average weighted rate of synthesis of 1,4-butanediol, calculated as follows:

Titre/32

"μ" corresponds to the average speed of attainment of OD$_{600\ nm}$=4 inside the bioreactor, calculated according to the following formula:

$$X = x_0 e^{\mu t}$$

where:
X=OD$_{600\ nm}$=4
$x_0$=initial OD$_{600\ nm}$ after inoculum
μ=growth rate
t=time necessary for attainment of OD$_{600\ nm}$=4.

In Table 1 the values of titre, yield, productivity and μ are normalized to the respective values of Example 1

TABLE 1

|  | TITRE | YIELD | PRODUCTIVITY | μ |
| --- | --- | --- | --- | --- |
| Example 1 (comparative) | 100.0 | 100.0 | 100.0 | 100.0 |
| Example 2 (comparative) | 84.9 | 91.0 | 85.9 | 119.3 |
| Example 3 | 108.3 | 106.7 | 108.3 | 127.2 |

It appears, therefore, that the culture medium comprising the glucose/saccharose mixture (according to the invention) allows the synthesis of 1,4-butanediol with better performance levels than those of both glucose and of saccharose.

Examples 4-9

The fermentation process of Example 1 was repeated using, instead of glucose, the following sugar mixtures (see Table 2).

TABLE 2

COMPOSITION OF THE SUGAR MIXTURES USED IN EXAMPLES 4-9

| Example | glucose (wt %) | saccharose (wt %) |
| --- | --- | --- |
| 4 | 90 | 10 |
| 5 | 80 | 20 |
| 6 | 40 | 60 |
| 7 | 30 | 70 |
| 8 | 20 | 80 |
| 9 | 10 | 90 |

For each Example, three fermentation processes were performed, and the average Titre, Yield and Productivity and the growth rate of the microorganisms (μ) (Table 3) were determined according to the formula above reported. In Table 3 the values of titre, yield, productivity and μ are normalized to the respective values of Example 1.

TABLE 3

| Example | TITRE | YIELD | PRODUCTIVITY | μ |
|---|---|---|---|---|
| 4 | 103.4 | 99.4 | 103.4 | 132.2 |
| 5 | 103.6 | 98.5 | 103.6 | 131.5 |
| 6 | 109.9 | 106.5 | 109.9 | 131.0 |
| 7 | 107.3 | 108.2 | 107.3 | 133.3 |
| 8 | 99.2 | 101.8 | 99.1 | 141.9 |
| 9 | 94.0 | 98.2 | 94.0 | 139.5 |

The invention claimed is:

1. A process for the synthesis of 1,4-butanediol comprising fermentation of a culture medium by a microorganism belonging to the species *Escherichia coli*, provided with at least one metabolic pathway for the synthesis of 1,4-butanediol and able to use saccharose by means of at least one operon for the assimilation of saccharose, in which said culture medium comprises a glucose and saccharose mixture comprising, based on the combined weight of glucose and saccharose, 10-90% by weight of saccharose and 10-90% by weight of glucose, said operon being selected from the scr regulon from the *Escherichia coli* strain H155 or the regulon csc of the *Escherichia coli* strain W or both.

2. The process according to claim 1, further comprising:
   i. production of 1,4-butanediol; and
   ii. purification of the 1,4-butanediol obtained in step i.

3. The process according to claim 2, in which the concentration of said glucose and saccharose mixture in the culture medium is from 10 to 100 g/L.

4. The process according to claim 1, wherein the culture medium comprises sugars different from saccharose and glucose amount up to 20 wt % with respect to the total amount of sugars in the culture medium.

5. The process according to claim 1, in which during fermentation, the operating conditions are as follows: agitation rate=800–900 rpm, air flow 0.4–1 Pa*m$^3$/s, pH 6-7, temperature 30-37° C.

6. The process according to claim 1, in which said microorganism the metabolic pathway of synthesis of 1,4-butanediol has been created artificially.

7. The process according to claim 2, in which said step ii comprises the following steps:
   (ii-a) separation of a liquid phase containing 1,4-butanediol from one or more solid phases;
   (ii-b) purification of the liquid phase containing 1,4-butanediol.

8. The process according to claim 7, in which said step (ii-a) one or more treatments are carried out chosen from settling, centrifugation, filtration, microfiltration, nanofiltration, ultrafiltration, and osmosis.

9. The process according to claim 7, in which in said step (ii-b) one or more treatments are carried out chosen from among evaporation, distillation, and crystallization.

10. Process according to claim 7, in which said step (ii-b) comprises the steps of:
    (ii-b-1) separate, by means of heating, at least one vapour phase and at least one condensate;
    (ii-b-2) condense at least one part of said at least one vapour phase, obtaining a final composition essentially comprising 1,4-butanediol.

11. The process according to claim 1, wherein the glucose and saccharose mixture comprises, based on the combined weight of glucose and saccharose, 20-80% by weight of saccharose and 20-80% by weight of glucose.

12. The process according to 2, wherein the culture medium comprises sugars different from saccharose and glucose amount up to 20 wt % with respect to the total amount of sugars in the culture medium.

13. The process according to claim 3, wherein the culture medium comprises sugars different from saccharose and glucose amount up to 20 wt % with respect to the total amount of sugars in the culture medium.

14. The process according to claim 2, in which during fermentation, the operating conditions are as follows: agitation rate=800-900 rpm, air flow 0.4-1 Pa*m$^3$/s, pH 6-7, temperature 30-37° C.

15. The process according to claim 3, in which during fermentation, the operating conditions are as follows: agitation rate=800-900 rpm, air flow 0.4-1 Pa*m$^3$/s, pH 6-7, temperature 30-37° C.

16. The process according to claim 4, in which during fermentation, the operating conditions are as follows: agitation rate=800-900 rpm, air flow 0.4-1 Pa*m$^3$/s, pH 6-7, temperature 30-37° C.

17. The process according to claim 2, in which said microorganism the metabolic pathway of synthesis of 1,4-butanediol has been created artificially.

18. The process according to claim 3, in which said microorganism the metabolic pathway of synthesis of 1,4-butanediol has been created artificially.

19. The process according to claim 4, in which said microorganism the metabolic pathway of synthesis of 1,4-butanediol has been created artificially.

20. The process according to claim 5, in which said microorganism the metabolic pathway of synthesis of 1,4-butanediol has been created artificially.

* * * * *